US00PP32601P2

(12) United States Plant Patent
Hartman

(10) Patent No.: US PP32,601 P2
(45) Date of Patent: Dec. 8, 2020

(54) ***CALADIUM* PLANT NAMED 'WCH PK 158-22'**

(50) Latin Name: ***Caladium* X *hortulanum***
Varietal Denomination: WCH PK 158-22

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/873,506

(22) Filed: Apr. 23, 2020

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'WCH PK 158-22', characterized by its compact and mounding plant habit; dense and bushy appearance; vigorous growth habit and rapid growth rate; fancy-type leaves that are pink and purplish pink in color on a dark green-colored background with dark red to red purple-colored venation; and petioles that are tan to tannish pink in color.

4 Drawing Sheets

Figure 1:
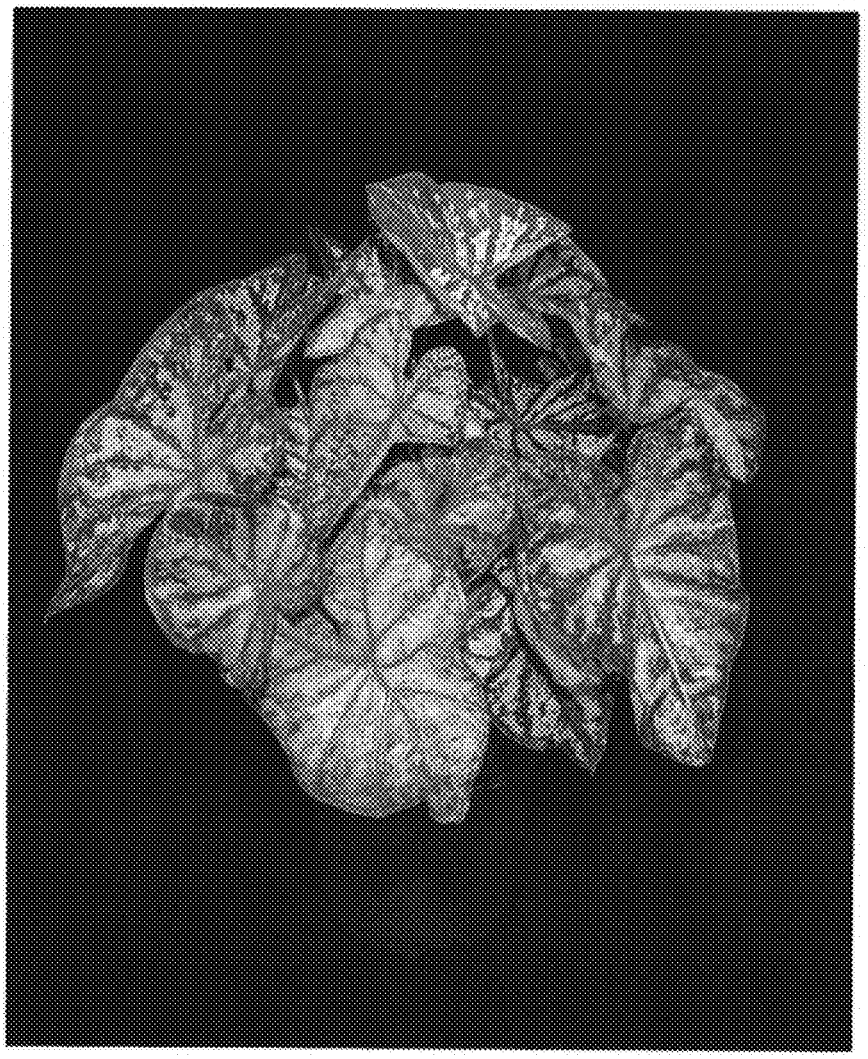

Botanical designation: *Caladium* X *hortulanum*.
Cultivar denomination: 'WCH PK 158-22'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'WCH PK 158-22'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* X *hortulanum* 'Summer Breeze', disclosed in U.S. Plant Pat. No. 25,420, as the female, or seed, parent with *Caladium* X *hortulanum* 'White Christmas', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WCH PK 158-22'. These characteristics in combination distinguish 'WCH PK 158-22' as a new and distinct *Caladium* plant:

1. Compact and mounding plant habit; dense and bushy appearance.
2. Vigorous growth habit and rapid growth rate.
3. Fancy-type leaves that are pink and purplish pink in color on a dark green-colored background with dark red to red purple-colored venation.
4. Petioles that are tan to tannish pink in color.

Plants of the new *Caladium* differ primarily from plants of the female parent, 'Summer Breeze', in the following characteristics:

1. Plants of the new *Caladium* and 'Summer Breeze' differ in leaf color as leaves of the new *Caladium* are pink and purplish pink in color on a dark green-colored background with dark red to red purple-colored venation whereas leaves of 'Summer Breeze' are creamy white in color with central pink-colored blush, pink-colored venation and green-colored margins.
2. Developing leaves of plants of the new *Caladium* are glossier than developing leaves of 'Summer Breeze'.

Plants of the new *Caladium* differ primarily from plants of the male parent, 'White Christmas', in the following characteristics:

1. Plants of the new *Caladium* are more compact and mounding than plants of 'White Christmas'.
2. Plants of the new *Caladium* are denser and bushier than plants of 'White Christmas'.
3. Plants of the new *Caladium* and 'White Christmas' differ in leaf color as leaves of the new *Caladium* are pink and purplish pink in color on a dark green-colored background with dark red to red purple-colored venation whereas leaves of 'White Christmas' have distinct dark green-colored venation with white-colored interveinal areas that are often tinged with pink and dark green-colored borders.

4. Plants of the new *Caladium* and 'White Christmas' differ in leaf petiole color as leaf petioles of the new *Caladium* are tan to tannish pink in color whereas leaf petioles of 'White Christmas' are green in color with close to black brown-colored stripes.

Plants of the new *Caladium* can be compared to plants of *Caladium* X *hortulanum* 'Pink Splash', disclosed in U.S. Plant Pat. No. 23,792. In side-by-side comparisons, plants of the new *Caladium* differ primarily from plants of 'Pink Splash' in the following characteristics:

1. Plants of the new *Caladium* are more compact and mounding than plants of 'Pink Splash'.
2. Plants of the new *Caladium* are denser and bushier than plants of 'Pink Splash'.
3. Plants of the new *Caladium* and 'Pink Splash' differ in leaf color as leaves of the new *Caladium* are pink and purplish pink in color on a dark green-colored background with dark red to red purple-colored venation whereas leaves of 'Pink Splash' have dark green-colored venation, red purple-colored interveinal areas and dark green-colored margins.

Plants of the new *Caladium* can also be compared to plants of *Caladium* X *hortulanum* 'Tapestry', disclosed in U.S. Plant Pat. No. 24,432. In side-by-side comparisons, plants of the new *Caladium* differ primarily from plants of 'Tapestry' in the following characteristics:

1. Plants of the new *Caladium* are more compact and mounding than plants of 'Tapestry'.
2. Plants of the new *Caladium* are denser and bushier than plants of 'Tapestry'.
3. Plants of the new *Caladium* and 'Tapestry' differ in leaf color as leaves of the new *Caladium* are pink and purplish pink in color on a dark green-colored background with dark red to red purple-colored venation whereas leaves of 'Tapestry' have rose pink-colored venation and white and pink-colored interveinal areas surrounded by olive green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 6) is a side perspective view of a typical plant of 'WCH PK 158-22' in a container and grown in a shade house (tuber de-eyed).

Figure 2:
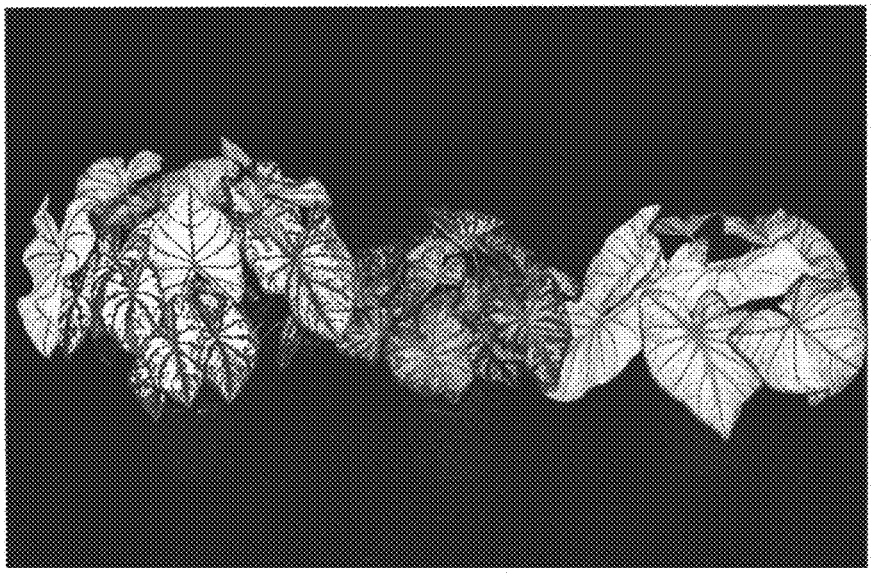

The photograph at the top of the second sheet (FIG. 2 of 6) is a comparison view of typical potted plants of the male parent, 'White Christmas' (left), 'WCH PK 158-22' (center) and the female parent, 'Summer Breeze' (right).

Figure 3:
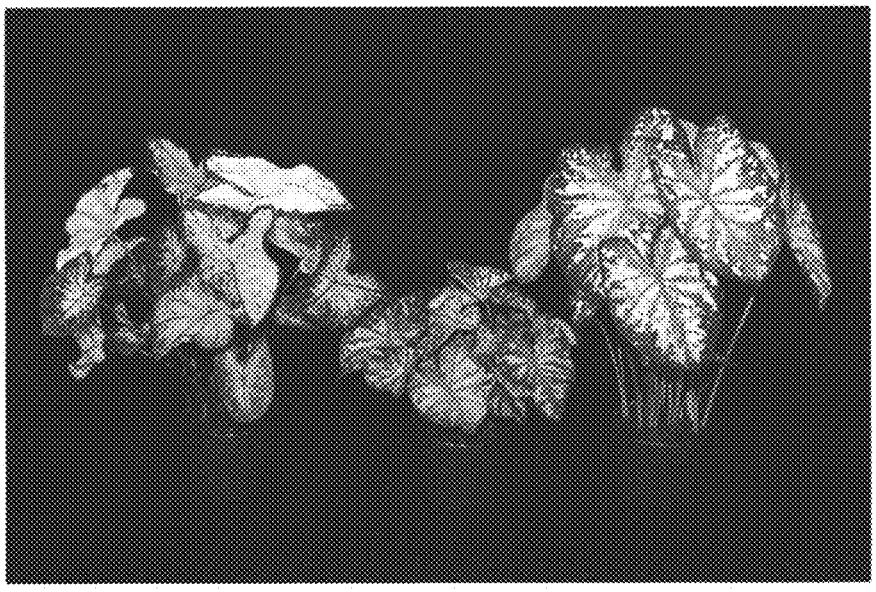

The photograph at the bottom of the second sheet (FIG. 3 of 6) is a comparison view of typical potted plants of 'Pink Splash' (left), 'WCH PK 158-22' (center) and 'Tapestry' (right).

Figure 4:
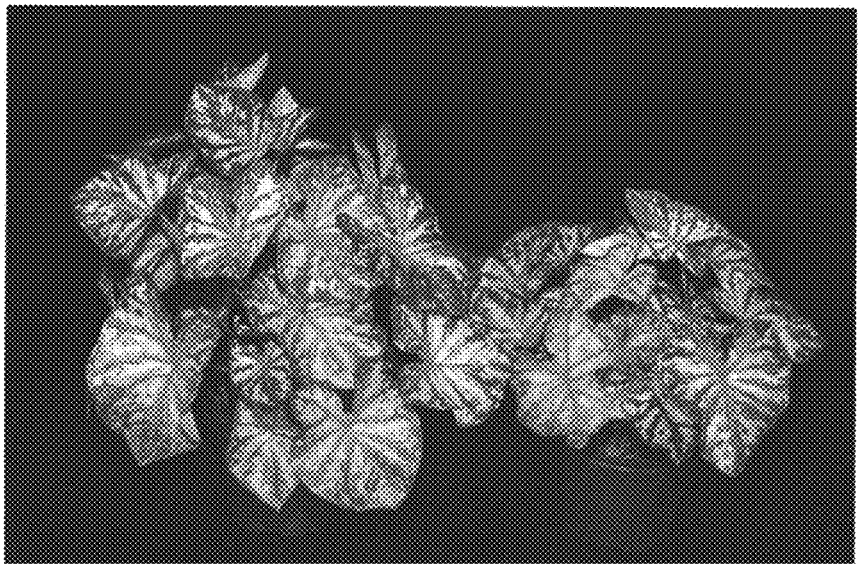

The photograph at the top of the third sheet (FIG. 4 of 6) is a comparison view of typical plants of 'WCH PK 158-22' grown in containers, the plant on the left has not had its tuber de-eyed and the plant on the right has had its tuber de-eyed prior to planting.

Figure 5:
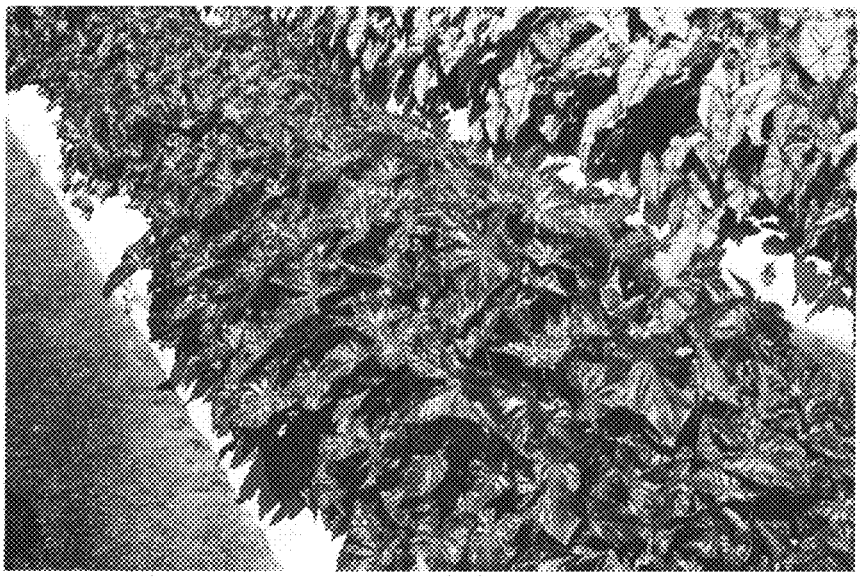

The photograph at the bottom of the third sheet (FIG. 5 of 6) is a side perspective view of typical plants of 'WCH PK 158-22' grown in an open production field.

Figure 6:
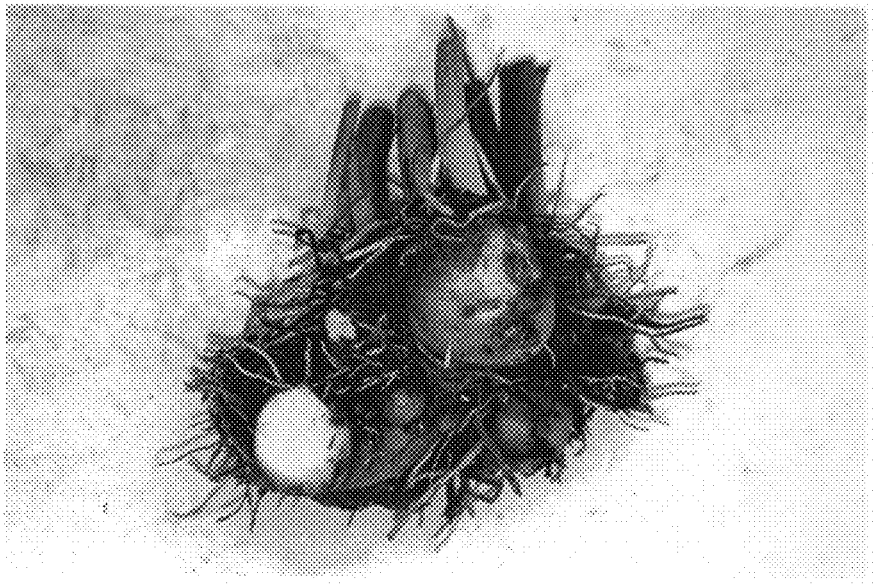

The photograph on the fourth sheet (FIG. 6 of 6) is a close-up view of typical freshly-harvested tubers with roots and leaf petioles of 'WCH PK 158-22'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were five weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'WCH PK 158-22'.

Parentage:

*Female, or seed, parent.*—*Caladium* X *hortulanum* 'Summer Breeze', disclosed in U.S. Plant Pat. No. 25,420.

*Male, or pollen, parent.*—*Caladium* X *hortulanum* 'White Christmas', not patented.

PROPAGATION:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments round to ovate in shape. Height: About 8.3 cm. Diameter: About 9 cm. Segment height: About 2.6 cm. Segment diameter: About 2.75 cm. Axillary bud shape: Roughly triangular. Axillary bud size: About 3 mm by 4 mm. Texture: Thick, starchy; somewhat brittle. Color: Periderm, freshly-harvested: Close to 199B. Periderm, dried: Close to 200A. Epidermis: Initially, close to 159B becoming closer to 159C and 159D with development. Cortical tissue: Close to 3D. Axillary buds: Close to 39B and 39C. Root description: Moderately thick, fleshy contractile roots with few lateral branches; color, close to NN155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Compact and mounding plant habit; dense and bushy appearance; vigorous growth habit and rapid growth rate; potted plants finish in saleable form in about five to six weeks after planting tubers; leaf petioles and leaves arise from one or more growing points on tubers; leaf petioles initially upright and somewhat outwardly leaning with development.

*Plant height, shade house-grown potted plants*.—About 25 cm to 35.5 cm.

*Plant diameter or spread, shade house-grown potted plants*.—About 34 cm to 40 cm.

*Number of shoots per plant, shade house-grown potted plants, tubers not de-eyed*.—About eight to twelve develop per #1 tuber.

*Number of shoots per plant, shade house-grown potted plants, tubers de-eyed*.—About 13 to 14 develop per #1 tuber.

*Cataphylls, shade house-grown potted plants*.—Length: About 3.7 cm to 4.7 cm. Width: About 6 mm to 10 mm. Shape: Wedge or strap-shaped. Apex: Acute, obtuse or emarginate. Base: Sheathing the stem. Color, outer surface: Initially close to 177D tinged with close to 181C to 181D with stippling, streaks and faint tessellations of close to 200C and 182A; with development, color becoming closer to N199B and N199C faintly tinged with close to 187B. Color, inner surface: Close to 199D and 179B to 179C; colors and patterns on outer surface visible on inner surface.

Leaf description:

*Arrangement and type*.—Alternate; simple; fancy-type.

*Length, shade house-grown potted plants*.—About 11.5 cm to 20.5 cm.

*Width, shade house-grown potted plants*.—About 7.2 cm to 14 cm; when flattened, about 8.3 cm to 14.8 cm.

*Shape*.—Ovate, cordate.

*Apex*.—Acute or acuminate.

*Base*.—Sagittate-peltate, cordate.

*Margin*.—Entire; slightly undulate with broad undulations.

*Texture and luster, upper surface*.—Smooth, glabrous; initially glossy becoming dull with development.

*Texture and luster, lower surface*.—Smooth, glabrous; slightly glaucous and dull sheen.

*Venation pattern*.—Pinnate.

*Color, shade house-grown potted plants*.—Developing leaves, upper surface: Background color: Close to 147A with speckles, close to 155C and 65D. Towards the margins: Close to 147A with speckles, close to 155C and 65D. Leaf edge: Narrow, close to 183B. Basal notch: Close to 187B. Leaf attachment point: Close to 185D. Midvein and lateral venation: Close to 60A surrounded by close to 184B. Interveinal areas: Close to 147A, 51B, 51C, 51D and 65D. Random spots and blotches: Close to 53C and 51B. Developing leaves, lower surface: Background color: Close to 191A tinged with close to 189A and with speckles, close to N155C and 191D. Towards the margins: Close to 191A tinged with close to 189A and with speckles, close to N155C and 191D. Leaf edge: Narrow, close to 183A. Basal notch: Close to 187A. Leaf attachment point: Close to 187A. Midvein: Close to 199D streaked with close to 185B. Primary venation: Close to 196B and 196C streaked with close to 185B and surrounded by close to 60B. Interveinal areas: Close to 191D, 54B, 54C and 54D. Random spots and blotches: Close to 54A. Fully developed leaves, upper surface: Background color: Close to 147A with speckles, close to 155C, 50B and 50C. Towards the margins: Close to 147A with speckles, close to 155C, 50B and 50C. Leaf edge: Narrow, close to 187A. Basal notch: Close to 187B. Leaf attachment point: Close to 187B. Midvein and lateral venation: Close to 60A surrounded by close to 185A and 147A. Interveinal areas: Close to 65B, 65C and 65D with spots and blotches, close to 147A. Random spots and blotches: Close to 63A, 63B, 65A and 65B. Fully developed leaves, lower surface: Background color: Close to 191A with spots and speckles, close to 54C, 54D and 155C. Towards the margins: Close to 191A with spots and speckles, close to 54C, 54D and 155C. Leaf edge: Narrow, close to 187B. Basal notch: Close to 187B. Leaf attachment point: Close to 187B. Midvein: Close to 185B or close to 199D streaked with close to 185B surrounded by 60A. Primary venation: Close to 199D streaked with close to 185B and close to N148D streaked with close to 185B. Interveinal areas: Close to 54C, 54D, 191A and 191D. Random spots and blotches: Close to 54C and 54D.

*Petioles*.—Aspect: Initially upright and straight and leaning outwardly with development; flexible. Length, shade house-grown potted plants: About 14.5 cm to 25.5 cm. Diameter, distally, shade house-grown potted plants: About 3 mm to 4 mm. Diameter, proximally, shade house-grown potted plants: About 3.5 mm to 7 mm. Texture and luster: Smooth, glabrous; at the leaf junction, glaucous. Color, shade house-grown potted plants: When developing and fully developed: Close to 177D tinged with close to 181C to 181D with stippling and faint tessellations of close to 200A tinged with close to 147A; proximally, close to 177D with stippling, streaks and tessellations of close to 200B tinged with close to 147A; at the leaf junction, close to 181D flushed and streaked with close to 185A. Wing length, shade house-grown potted plants: About 4.8 cm to 6.5 cm. Wing diameter, shade house-grown potted plants: About 6.5 mm to 8 mm. Texture and luster, inner and outer surfaces: Smooth, glabrous; dull sheen. Wing color, shade house-grown potted plants: Outer surface: Close to N170D and N155C with stippling, streaks and tessellations of close to 200A tinged with close to 147A. Inner surface: Close to N155C to N155D; colors and patterns on the outer surface are visible on the inner surface.

Inflorescence description: To date, inflorescence development has not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'WCH PK 158-22' as illustrated and described.

* * * * *